United States Patent [19]

Nelson et al.

[11] 4,011,241
[45] Mar. 8, 1977

[54] AN INTERMEDIATE IN THE PREPARATION OF 2-(5H-DIBENZO[a,d]CYCLOHEPTEN-5-ON-2-YL)ACETIC, PROPIONIC AND BUTYRIC ACIDS

[75] Inventors: Peter H. Nelson; Karl G. Untch, Los Altos, Calif.

[73] Assignee: Syntex (U.S.A.) Inc., Palo Alto, Calif.

[22] Filed: Sept. 8, 1975

[21] Appl. No.: 611,053

[52] U.S. Cl. .............................. 260/348 R; 260/141; 260/338; 260/340.7; 260/340.9; 260/465 R; 260/469; 260/475 R; 260/515 R; 260/544 B; 260/615 A

[51] Int. Cl.[2] ...................................... C07D 303/02

[58] Field of Search ................... 260/348 R, 340.9

[56] References Cited

UNITED STATES PATENTS

| | | | |
|---|---|---|---|
| 3,833,655 | 9/1974 | Edenhofer et al. | 260/340.9 |
| 3,845,093 | 10/1974 | Rey-Bellet et al. | 260/465 F |

*Primary Examiner*—Ethel G. Love
*Attorney, Agent, or Firm*—Alan M. Krubiner; William B. Walker

[57] ABSTRACT

2-(5H-Dibenzo[a,d]cyclohepten-5-on-2-yl)acetic, propionic and butyric acids, are prepared from glycidonitrile intermediates. The acid products exhibit anti-inflamatory, analgesic and anti-pyretic activity.

2 Claims, No Drawings

AN INTERMEDIATE IN THE PREPARATION OF 2-(5H-DIBENZO[A,D]CYCLOHEPTEN-5-ON-2-YL)ACETIC, PROPIONIC AND BUTYRIC ACIDS

DETAILED DESCRIPTION OF THE INVENTION

The present invention is concerned with a process for the preparation of 2-(5H-dibenzo[a,d]cyclohepten-5-on-2-yl) acetic, propionic and butyric acids, and salts thereof. More specifically, the present invention concerns processes for the preparation of the compounds of the formula

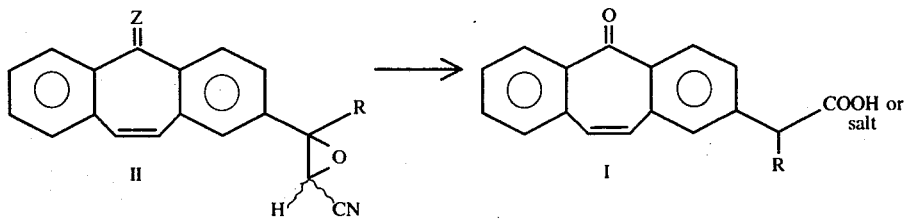

or a salt thereof, wherein R is hydrogen, methyl or ethyl.

The compounds of Formula I exhibit anti-inflammatory, analgesic and anti-pyretic activity. Accordingly, compounds of Formula I and compositions containing same are useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the compounds of Formula I are useful for the relief of these conditions as well as the inflammation.

The compounds of Formula I are also uterine smooth muscle relaxants and thus are useful as agents for maintaining the pregnancy of pregnant mammals, for the benefit of the mother and/or the fetus, until termination of the pregnancy is considered, from a medical point of view, to be favorable, or more favorable, for the mother and/or the fetus.

Salts of the carboxylic acids of Formula I refer to those salts prepared from inorganic and organic bases. Salts derived from inorganic bases include the alkali metal salts such as sodium, potassium and lithium; the alkaline earth salts such as calcium and magnesium; as well as the ammonium and copper salts. Those salts derived from organic bases include the ethanolamine, diethylamine, tris(hydroxymethyl)aminomethane, choline, caffeine, and lysine salts. A preferred subclass of salts of Formula I are those prepared from pharmaceutically acceptable, non-toxic bases.

The term "conventional ketal protecting group" refers to those ketal groups conventionally used in the art to protect a reactive ketone function, which groups are readily removable by acid hydrolysis. Classes of conventional ketal protecting groups contemplated by the above are dialkyl ketals (alkyl groups of from 1 to 6 carbon atoms) such as for example, dimethyl or diethyl ketals; alkylene ketals (alkylene of 2 to 4 carbon atoms optionally substituted with lower alkyl groups of from 1 to 4 carbon atoms) such as for example, the ethylene, 1,3-propylene, 2,2-dimethyl-1,3-propylene, 1,4-butylene and 2,3-butylene ketals; and dibenzyl ketals.

The process of the present invention may be summarized as follows:

wherein R is as above and Z is oxo or a conventional ketal protecting group.

Generally, the process of the present invention involves the conversion of a glycidonitrile intermediate of Formula II to a free acid of Formula I or a salt thereof. Such conversions are generally known in the art and a detailed description of an analogous conversion may be found, for example, in published Japanese Pat. Application No. 49055622.

The process of the present invention may be accomplished by opening of the epoxide ring of the glycidonitrile to afford either a cyanoketone or a cyanohalohydrin, which is further converted to an acid of Formula I, or salt thereof.

In these reactions, the starting materials and reagents may be contacted in any convenient manner and maintained at a temperature and for a period of time sufficient to complete the desired reaction. Furthermore the reaction product may be isolated and recovered from the reaction using, as in the case of the reaction conditions themselves, procedures conventionally used in the art for conducting such reactions or analogous reactions.

In one embodiment of the present process the starting glycidonitrile of Formula II is treated with a hydrogen halide such as, for example, hydrogen chloride or hydrogen bromide to afford an intermediate cyanohalohydrin. This reaction is carried out in the presence or absence of water. When water is present, a starting ketal group may be hydrolyzed to the corresponding free ketone. This portion of the reaction may be carried out at a temperature of from about 20° to about 60° C.

In the next step, the intermediate cyanohalohydrin is treated with an acylating agent such as, for example, an acid anhydride or an acid halide such as acetic anhydride or acetyl chloride, in the presence of a tertiary amine such as pyridine or triethylamine at a temperature between about 0° to about 60° C. Subsequently, dehydrohalogenation may be accomplished by the addition of an excess of base such as, for example, an amine base used for the above acylation step, or another base such as, for example, sodium hydride, sodium amide, potassium t-butoxide, and the like.

The enol acylate thus formed is subjected to hydrolysis under basic conditions. Suitable bases include aqueous alkali metal hydroxides such as, for example, sodium or potassium hydroxide, optionally in the presence of a water miscible organic solvent such as an alcohol or acetone.

Completion of this reaction affords a solution containing the salt of the carboxylic acid of Formula I. This salt may be isolated from the reaction mixture by, for example, evaporation of the solvent and crystallization or, preferably, the alkali metal salt is converted to the free acid by acidification with a strong acid such as, for example, hydrochloric acid or sulfuric acid. The free carboxylic acid may then be isolated by extraction, recrystallization, and the like.

In another embodiment of the process of the present invention the starting glycidonitrile of Formula II is converted to a cyanoketone by treatment with a nonnucleophilic Lewis acid such as for example, potassium bisulfate, lithium trifluoroacetate, lithium perchlorate, and the like. This reaction may be carried out in an inert organic solvent such as, for example, a hydrocarbon, e.g. benzene, toluene, and the like. The reaction may be carried out at a temperature between 50° to 150° C.

The cyanoketone may then be converted to the alkali metal salt of the acid of Formula I by hydrolysis with a base such as an alkali metal hydroxide, e.g. sodium hydroxide, in the presence of water. This hydrolysis reaction may be carried out at a temperature between about 20° and about 120° C.

As mentioned above, the alkali metal salt may be isolated directly from the reaction mixture or, preferably, is converted to the free acid by acidifying with a strong acid.

While intermediate reaction products may be isolated, it is preferred to conduct the above mentioned reactions so as not to isolate or purify reaction intermediates, and only to isolate and purify the final acid or salt of Formual I.

The starting materials for the present process may be prepared as follows:

2-methylterephthalic acid is esterified with methanol, in the presence of an acid catalyst, to afford the corresponding dimethyl ester which, in turn, is reacted with N-bromosuccinimide to afford 2-bromomethylterephthalic acid dimethyl ester. This diester is reacted with triphenylphosphine to afford a 2,5-bis(carbomethoxy)-benzyltriphenylphosphonium bromide which is treated with benzaldehyde and diazabicyclononene to afford, after alkaline hydrolysis, cis and trans-stilbene 2,5-dicarboxylic acid. Hydrogenation of this latter compound with hydrogen over a 5% palladium on carbon catalyst affords 2-(2-phenethyl)terephthalic acid. Treatment with polyphosphoric acid yields 5-oxo-5H-dibenzo [a,d]cycloheptane-2-carboxylic acid.

5-Oxo-5H-dibenzo[a,d]cycloheptene-2-carboxylic acid is prepared by successively treating the above compound with diazomethane, N-bromosuccinimide, and dimethylformamide/diazabicyclononene, followed by base hydrolysis and acidification.

This acid may be converted to the methyl ketone by conversion to the acid chloride with thionyl chloride, conversion of the acid chloride to the diazoketone by reaction with diazomethane, and treatment of the diazoketone with hydriodic acid.

The glycidonitrile may be prepared from the methyl ketone by reaction with chloroacetonitrile in the presence of a base such as sodium methoxide.

The ethyl ketone and corresponding glycidonitrile (R is ethyl) intermediate may be prepared in the same manner, substituting diazoethane for diazomethane.

The aldehyde may be prepared by conversion of the carboxylic acid to its methyl ester by, for example, reaction of the acid chloride with methanol, reduction to the diol with lithium aluminum hydride and reoxidation to the keto aldehyde with manganese dioxide. Conversion to the glycidonitrile (R is hydrogen) is as described above.

Ketal protected glycidonitriles may be prepared by first ketalizing the corresponding aldehyde, methyl ketone or ethyl ketone by reaction with phosphorus pentachloride followed by triethylamine and, for example, ethylene glycol, followed by reaction with chloroacetonitrile. The glycidonitriles of Formula II exist in two stereoisomeric forms, a cis-form and a trans-form. Both of these forms, as well as mixtures thereof, afford the desired final products of Formula I.

The following examples illustrate preferred embodiments of the processes of the present invention. They should not be construed as limiting the scope or spirit of the invention in any manner. The yields of product obtained from the present process vary, depending upon the choice of starting material, reagents, reaction conditions, and workup. Generally, however, the yields are in the range of from 5 to about 50 percent.

PREPARATION 1

148 G. of 2-methylterephthalic acids is refluxed for 24 hours in 750 ml. of dry methanol containing 30 ml. of sulfuric acid. The solution is cooled, poured into water and extracted with ether. The extract is washed, dried and evaporated to give dimethyl-2-methylterephthalate.

88 G. of dimethyl-2-methylterephthalate in 1000 ml. of carbon tetrachloride containing 89 g. (1 eq.) of N-bromosuccinimide is refluxed for 3 hours using a heat lamp. The solution is cooled, filtered and evaporated to dryness to give dimethyl-2-bromomethyl-terephthalate.

25.7 G. of dimethyl-2-bromomethylterephthalate is refluxed in 250 ml. of acetonitrile containing 26.2 g. (1 eq.) of triphenylphosphine for 4 hours. The solution is cooled and diluted with 1250 ml. of ether thereby precipitating 2,5-bis(carbomethoxy)-benzyltriphenylphosphonium bromide which is filtered off and dried under vacuum.

51.9 G. of 2,5-bis(carbomethoxy)-benzyltriphenylphosphonium bromide and 10.6 g. of benzaldehyde are stirred in 300 ml. of acetonitrile and 12.4 g. of diazabicyclononene is added. The mixture is heated briefly to reflux, then cooled and evaporated to an oil. The oil is dissolved in ethyl acetate, and the solution washed with dilute hydrochloric acid, dried and evaporated. The residue is refluxed for 12 hours, in a solution of 20 g. of potassium hydroxide in 200 ml. of water and 50 ml. of methanol. The solution is cooled and extracted with chloroform. The aqueous solution is acidified with dilute hydrochloric acid and the precipitated cis and trans stilbene-2,5-dicarboxylic acid is filtered off and dried.

23.6 G. of cis and trans -stilbene-2,5-dicarboxylic acid is dissolved in 100 ml. of dimethylformamide containing 500 mg. of 5% palladium on carbon and hydrogenated for 2 hours. The solution is filtered and evaporated to dryness to give a crude product which upon recrystallization from aqueous ethanol yields 2-(2-phenethyl)terephthalic acid.

23.8 G. of 2-(2-phenethyl)terephthalic acid is dissolved in 200 ml. of sulpholane at 130° C. and 150 ml.

of polyphosphoric acid is added with stirring. The mixture is stirred at 130° C. for 4 hours, then poured into 1000 ml. of water. The product is filtered off and recrystallized from aqueous dimethylformide to yield 5-oxo-5H-dibenzo[a,d]cycloheptane-2-carboxylic acid (m.p. 203°–204° C.).

PREPARATION 2

5.0 G. of 5-oxo-5H-dibenzo[a,d]cycloheptane-2-carboxylic acid (as prepared in Preparation 1 above) is suspended in 50 ml. of dioxane, added to excess ethereal diazomethane, and stirred until dissolution is complete. The solution is then evaporated to dryness to yield 2-carbomethoxy-5-oxo-5H-dibenzo[a,d]cycloheptane.

4.68 G. of 2-carbomethoxy-5-oxo-5H-dibenzo[a,d]cycloheptane is refluxed in 100 ml. of carbon tetrachloride containing 3.56 g. (1 eq.) of N-bromosuccinimide while being irradiated with a 100 watt incandescent lamp. After 2 hours the solution is cooled, filtered and evaporated to dryness. The residue is dissolved in 30 ml. of dimethylformamide and 2.48 g. (1 eq.) of 1,5-diazabicyclo[3.4.0]nonene-5 is added. The mixture is heated briefly to 60° C., and water and ethyl acetate are added. The organic layer is washed with dilute hydrochloric acid and water, then dried and evaporated to give 2-carbomethoxy-5-oxo-5H-dibenzo[a,b]cycloheptene. Hydrolysis in eight to one aqueous methanol: 5% potassium hydroxide, followed by acidification with dilute hydrochloric acid yields 5-oxo-5H-dibenzo[a,d]cycloheptene-2-carboxylic acid (m.p. 261°–262° C.).

PREPARATION 3

A. 22 G. of 5-oxo-5H-dibenzo[a,d]cycloheptene-2-carboxylic acid is stirred in 200 ml. of chloroform, 50 ml. of thionyl chloride and 1 ml. of dimethylformamide for 8 hours. The mixture is evaporated to dryness and the residue recrystallized from acetonitrile to yield 2-chloroformyl-5-oxo-5H-dibenzo[a,d]cycloheptene.

B. 4.5 Gm. of 2-chloroformyl-5-oxo-5H-dibenzo[a,d]cycloheptene dissolved in 200 ml. of chloroform is added to an ice-cooled ethereal solution of diazomethane (from 15 gm. of N-nitroso-N-methyl urea). The mixture is stirred for two hours then evaporated to dryness to give 2-diazoacetyl-5H-dibenzo[a,d]cyclohepten-5-one. This compound is dissolved in 200 ml. of chloroform and the solution is cooled to O° and 5 ml. of 57% aqueous hydriodic acid is added. The mixture is stirred for 30 minutes and then water is added and the chloroform layer is washed with aqueous sodium thiosulfate, the dried and evaporated. The residue is recrystallized from methanol to afford 1.55 gm., 30%, of 2-acetyl-5H-dibenzo[a,d]cyclohepten-5-one, m.p. 128°–130° C.

PREPARATION 4

The acid chloride from Preparation 3A is converted to the methyl ester by reaction with methanol and triethylamine. 2.0 Gm. of methyl 5H-dibenzo[a,d]cyclohepten-5-one-2-carboxylate is dissolved in 200 ml. of ether and 0.5 gm. of lithium aluminium hydride is added. The reaction is refluxed for two hours then cooled and the excess reducing agent is decomposed by addition of water. The solution is filtered and to the filtrate is added 15.0 gm. of manganese dioxide. The mixture is stirred for 16 hours then filtered and evaporated to give a 50% yield of 2-formyl 5H-dibenzo[a,d]cyclohepten5-one, m.p. 149°–152° C.

PREPARATION 5

0.50 Gm. of 2-acetyl-5H-dibenzo[a,d]cycloheptene-5-one and 0.45 gm. of phosphorus pentachloride are stirred in 50 ml. of dry benzene for one hour, and then the solution is added to a mixture of 1.01 gm. of triethylamine, 1.35 gm. of ethylene glycol and 100 ml. of acetonitrile. The mixture is stirred for 20 hours then added to water and ether. The ethereal layer is washed with water, dried and evaporated to give a nearly quantitative yield of 5,5-ethylenedioxy-2-acetyl-5H-dibenzo[a,d]cycloheptene.

Use of 2-formyl-5H-dibenzo[a,d]cyclohepten-5-one gives a similar yield of 5,5-ethylenedioxy-2-formyl-5-H-dibenzo [a,d]cycloheptene.

PREPARATION 6

0.543 Gm. of 2-acetyl-5H-dibenzo[a,d]cyclohepten-5-one is dissolved in 20 ml. of tetrahydrofuran and the solution is cooled to 0° C. 0.18 Ml. of chloroacetonitrile is added followed by 0.14 gm. of sodium methoxide. After 2 hours the solution is added to water and extracted with ether. The ether solution is washed, dried and evaporated to give a product which, upon chromatography on silica gel, eluting with 1:1 hexan:ether, affords both isomers of 2,3-oxido-3-(5H-dibenzo[a,d]cyclohepten-5-on-2-yl)butyronitrile as follows: less polar isomer, 0.17 gm., 27%, m.p. 113°–115° C., more polar isomer, 0.08 gm., 12%, m.p. 137°–142° C.

Use of 2-formyl-5H-dibenzo[a,d]cyclohepten-5-one affords a similar yield of both isomers of 2,3-oxido-3-(5H-dibenzo[a,d]cyclohepten-5-on-2-yl)propionitrile.

Use of 5,5-ethylenedioxy-2-acetyl-5H-dibenzo[a,d]cycloheptene gives a similar yield of both isomers of 2,3-oxido3-(5,5-ethylenedioxy-5H-dibenzo[a,d]cyclohepten-2-yl)butyronitrile.

EXAMPLE 1

0.2 Gm. of 2,3-oxido-3-(5H-dibenzo[a,d]cyclohepten-5-on-2-yl)butyronitrile is dissolved in 20 ml. of benzene and hydrogen chloride is passed in for 5 minutes. After one hour a stream of nitrogen was passed in for 5 minutes. 0.118 Gm. of pyridine and 0.107 gm. of acetic anhydride are added and the mixture was left for 3 hours, at which time 0.15 gm. of triethylamine is added and the mixture is refluxed for 3 hours. A solution of 0.8 gm. of sodium hydroxide in 20 ml. of water is added and the reaction is refluxed a further two hours. The mixture containing sodium 2-(5H-dibenzo[a,d]cyclohepten-5-on-2-yl)propionate is cooled and the aqueous layer is separated and acidified with dilute hydrochloric acid, then extracted with ethyl acetate. The extract is washed, dried and evaporated to give 0.102 gm., 52%, of 2-(5H-dibenzo[a,d]cyclohepten-5-on-2-yl)propionic acid, m.p. (chloroform-hexane) 138°14 139° C.; m.p. (acetone-hexane) 113°–115° C.

Use of 2,3-oxido-3-(5H-dibenzo[a,d]cyclohepten-5-on-2-yl)propionitrile gives a similar yield of 2-(5H-dibenzo[a,d]cyclohepten-5-on-2-yl)acetic acid, m.p. (acetonehexane) 148°–149.5° C.

EXAMPLE 2

0.25 Gm. of 2,3-oxido-3(5,5-ethylenedioxy5H-dibenzo[a,d]cyclohepten-5-on-2-yl)butyronitrile is dissolved in 25 ml. of benzene containing 0.2 ml. of water. Hydrogen chloride is passed in for 5 minutes. After 3 hours a stream of nitrogen is passed in for 5 minutes. 1.0 ml. of pyridine and 0.5 ml. of acetic anhydride are added and the mixture is left for 3 hours, at which time 1.0 ml. of triethylamine is added, and the mixture is refluxed for 2 hours. A solution of 0.8 gm. of sodium hydroxide in 20 ml. of water is added and the mixture is refluxed a further 2 hours. The mixture is cooled and the aqueous layer is separated and acidified with dilute hydrochloric acid, then extracted with ethyl acetate. The extract is washed, dried and evaporated to afford 0.10 gm., 40% of 2-(5H-dibenzo[a,d]cyclohepten-5-on-2-yl)propionic acid, m.p. (chloroform-hexane) 138°–139° C.; m.p. (acetone-hexane) 113°–115° C.

What is claimed is:

1. A compound represented by the formula

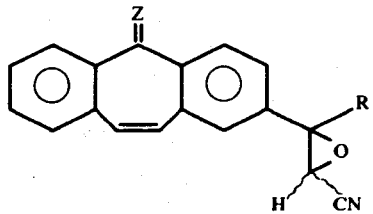

wherein R is hydrogen, methyl or ethyl and Z is oxo.

2. The compound of claim 1 which is 2,3-oxido-3-(5H-dibenzo[a,d]cyclohepten-5-on-2-yl)butyronitrile.